United States Patent [19]

Sherry et al.

[11] Patent Number: 5,429,773
[45] Date of Patent: Jul. 4, 1995

[54] PROCESS TO IMPROVE ALKYL ESTER SULFONATE SURFACTANT COMPOSITIONS

[75] Inventors: Alan E. Sherry; Benjamin E. Chapman; Michael T. Creedon, all of Cincinnati, Ohio

[73] Assignee: The Procter & Gamble Company, Cincinnati, Ohio

[21] Appl. No.: 14,192

[22] Filed: Feb. 5, 1993

[51] Int. Cl.⁶ ............................................. C10D 1/22
[52] U.S. Cl. .................... 252/554; 252/557; 554/88; 554/96; 554/98; 554/100; 554/97; 560/150
[58] Field of Search .............. 252/554, 557; 554/88, 554/96, 98, 100, 97; 560/150

[56] References Cited

U.S. PATENT DOCUMENTS

| | | | |
|---|---|---|---|
| 1,081,775 | 12/1913 | Russ | 554/100 |
| 2,078,516 | 4/1937 | Tulleners | 554/100 |
| 2,127,641 | 8/1938 | Cremer | 554/100 |
| 2,266,843 | 12/1941 | Beach | 554/100 |
| 3,159,657 | 12/1964 | Wulff et al. | 554/98 |
| 3,251,868 | 5/1966 | Stein et al. | 554/98 |
| 3,377,290 | 4/1968 | Stein et al. | 252/557 |
| 3,452,064 | 1/1965 | Stein et al. | 554/98 |
| 3,485,856 | 12/1969 | Wulff et al. | 546/156 |
| 3,777,290 | 4/1968 | Stein et al. | 334/15 |
| 3,997,575 | 12/1976 | Ogoshi et al. | 554/97 |
| 3,997,576 | 12/1976 | Oghoshi et al. | 554/98 |
| 4,080,372 | 3/1978 | Stein et al. | 554/96 |
| 4,217,289 | 8/1980 | Boehmer | 554/100 |
| 4,344,889 | 8/1982 | Inchauspe | 554/96 |
| 4,390,474 | 6/1983 | Nussbaum et al. | 562/33 |
| 4,404,143 | 9/1983 | Sekiguchi et al. | 560/149 |
| 4,495,092 | 1/1985 | Schmid et al. | 252/559 |
| 4,532,076 | 7/1985 | Schmid et al. | 252/557 |
| 4,545,939 | 10/1985 | Sekiguchi et al. | 554/98 |
| 4,547,318 | 10/1985 | Kloetzer et al. | 554/100 |
| 4,671,900 | 6/1987 | Schmid et al. | 554/88 |
| 4,695,409 | 9/1987 | Piorr et al. | 554/88 |
| 4,820,451 | 4/1989 | Piorr et al. | 554/88 |

FOREIGN PATENT DOCUMENTS 0153036 8/1985 European Pat. Off. .
3334517 4/1984 Germany .
53-027603 3/1978 Japan .
59-016870 1/1984 Japan .
59-025368 2/1984 Japan .
59-025369 2/1984 Japan .
58-197004 5/1985 Japan .
63-105097 5/1988 Japan .
63-254198 10/1988 Japan .
1-256597 10/1989 Japan .
0290842 11/1990 Japan .
290842 11/1990 Japan .
58-45996 10/1993 Japan .
4589 5/1990 WIPO .
WO93/05013 3/1993 WIPO .

OTHER PUBLICATIONS

Stein and Baumann, α–Sulfonated Fatty Acids and Esters: Manufacturing Process, Properties, and Applications, JAOCS 52, pp. 323–329 (1975) no month available.
Connor, Identification of Certain Sultones as the Sensitizers in an Alkyl Ethoxy Sulfate, "Fette Seifen Anstrichmittel" 77, 25–29 (1975) no month available.

*Primary Examiner*—Paul Lieberman
*Assistant Examiner*—Necholus Ogden
*Attorney, Agent, or Firm*—Michael D. Jones; Jerry J. Yetter; Jacobus C. Rasser

[57] ABSTRACT

A process for improving the color and purity of dark-colored potassium or magnesium alkyl ester sulfonate surfactant compositions, and particularly alpha-sulfo fatty acid methyl ester compositions, without the need for bleaching or other process steps. The process comprises the steps of (1) forming a mixture comprising (i) an alkyl ester sulfonate surfactant composition containing impurities including dark-colored impurities, organic and inorganic salts, and disalts, and (ii) water, and (2) separating the ester sulfonate surfactant from the mixture. The process may further comprise step (3) recovering the alkyl ester sulfonate surfactant. Methyl ester sulfonate surfactant compositions are most preferred. After processing in accordance with the invention, the alkyl ester sulfonate surfactant composition has improved color, purity, and odor properties.

37 Claims, No Drawings

PROCESS TO IMPROVE ALKYL ESTER SULFONATE SURFACTANT COMPOSITIONS

FIELD OF INVENTION

The invention is directed to improving the purity and color of certain potassium and magnesium alkyl ester sulfonate surfactant compositions, particularly alpha-sulfonated fatty acid methyl ester surfactant compositions. The process improves these surfactant compositions by removing impurities, formed during the preparation of the surfactants including dark-colored impurities, organic and inorganic salts, disalts, and soaps thereby resulting in higher purity surfactant compositions having improved color.

BACKGROUND OF THE INVENTION

The manufacture of alkali metal salts of alpha-sulfo fatty acid alkyl esters alternatively referred to as sulfonated fatty acid alkyl esters, alkyl ester- sulfonates, etc.) via neutralization of fatty acid ester sulfonic acids with aqueous caustic is well known. Such ester sulfonates are predominantly used as surfactants in washing and cleansing agents and products.

The known processes for making these ester sulfonates in good yields suffer from the formation of certain impurities including dark-colored impurities, organic and inorganic salts, and disalts. The ester sulfonic acids, from which the alkyl ester sulfonates are derived, are obtained by sulfonating fatty acid esters or, less preferably, by sulfonating and esterifying fatty acids. In order to obtain high sulfonation yields, excess sulfonating agent in combination with greater processing times and/or temperatures is required. These conditions can result in undesirable side reactions including the formation of the dark-colored impurities and the acid forms of organic and inorganic sulfate salts, and disalts. Examples of such sulfonation processes are described in U.S. Pat. Nos. 3,485,856 (Wulff et al.); 4,695,409 (Piorr et al.); and 4,820,451 (Piorr et al.); German Patent Application 3 535 184 (Imamura et al.); Japanese Laid Open Patent Publication Number 290842/90 (Application Number 113423/89); and "The Journal of the American Oil Chemists Society", 52 (1975), pp. 323–329.

For aesthetic and other reasons, dark-colored ester sulfonate compositions are not suitable for use directly in washing or cleansing agents and products. Therefore, the dark ester sulfonate products have heretofore been bleached in order to lighten their color. Typically, the dark products are treated with an aqueous bleaching agent, such as hydrogen peroxide or hypochlorite, before and/or after neutralization. Such bleaching processes are described in U.S. Pat. Nos. 3,159,657 (Wulff et al.); 3,452,064 (Stein et al.); 4,547,318 (Kloetzer et al.); 4,671,900 (Schmid et al.); and 4,874,552 (Richtler et al.).

The art has recognized certain inherent problems in the bleaching process, particularly handling difficulties, hydrolysis of the ester group, and formation of sensitizers. Heretofore, these problems have been dealt with, inter alia, by optimizing the bleaching process itself, or by modifying the ester sulfonation process itself to deliver an ester sulfonate with less color and/or fewer impurities. This allows for the use of milder bleaching conditions which may mitigate the problems associated with bleaching processes. Such processes are described in U.S. Pat. Nos. 3,997,576 (Oghoshi et al.); 4,080,372 (Stein et al.); 4,547,318 (Kloetzer et al.); and 4,671,900 (Kloetzer et al.). However, none of these references disclose a process for making ester sulfonate surfactant which is completely satisfactory.

A method of improving the color and purity of potassium and magnesium alkyl ester sulfonate surfactant compositions without the need for bleaching has now been discovered. More specifically, it has been discovered that a lighter-colored, higher purity alkyl ester sulfonate surfactant can be separated from a mixture comprising water and a dark-colored alkyl ester sulfonate surfactant composition. Upon forming a mixture comprising the ester sulfonate surfactant composition and water, the impurities, including dark-colored impurities, are solubilized and the alkyl ester sulfonate surfactant can be separated and recovered from the mixture to yield a product with improved, i.e., lighter, color. The recovered surfactant is also of improved purity, i.e., the recovered surfactant contains a lower level of organic and inorganic salt, disalt, and soap impurities. The process also provides an ester sulfonate surfactant having improved surfactant odor.

SUMMARY OF THE INVENTION

The present invention involves a novel process for improving an alkyl ester sulfonate (hereinafter ester sulfonate) surfactant composition, said surfactant composition comprising:

(i) an alkyl ester sulfonate surfactant having the general formula:

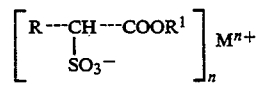

wherein: (1) R is on the average a $C_{10}$ to $C_{22}$, preferably a $C_{14}$ to $C_{16}$ alkyl, $R^1$ is on the average a $C_1$ to $C_8$, preferably $C_1$ alkyl and n is 1 when M is potassium; or (2) R is on the average a $C_{14}$ to $C_{22}$, preferably a $C_{14}$ to $C_{16}$ alkyl, $R^1$ is on the average a $C_1$ to $C_8$, preferably $C_1$ alkyl and n is 2 when M is magnesium; and (ii) impurities formed during the preparation of said alkyl ester sulfonate surfactant;

said process comprising the steps of:

(1) forming a mixture comprising:
   (a) said alkyl ester sulfonate surfactant composition; and
   (b) water in an amount sufficient to substantially solubilize said impurities; and
(2) separating said alkyl ester sulfonate surfactant from said mixture.

The invention is particularly significant for improving the color and purity of potassium methyl ester sulfonate surfactant compositions. The resultant product of the novel process herein exhibits good color quality, i.e. contains lower levels of dark-colored impurities, and also contains a reduced level of other undesirable impurities including soaps, organic and inorganic sulfate salts, disalts, etc.

DETAILED DESCRIPTION OF THE INVENTION

The ester sulfonate surfactant compositions which are improved in color and purity by the invention herein comprise ester sulfonates having the general formula (I):

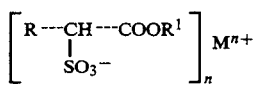

$$\left[ \begin{array}{c} R\text{---}CH\text{---}COOR^1 \\ | \\ SO_3^- \end{array} \right]_n M^{n+} \quad (I)$$

wherein R is on the average a $C_{10}$ to $C_{22}$ linear or branched alkyl chain, $R^1$ is on the average a $C_1$ to $C_8$ alkyl and n is 1 when M is potassium; or wherein R is on the average a $C_{14}$ to $C_{22}$ linear or branched alkyl chain, $R^1$ is on the average a $C_1$ to $C_8$ alkyl and n is 2 when M is magnesium.

Particularly useful ester sulfonates are those wherein $R^1$ is —$CH_3$, i.e. methyl ester sulfonates, and more particularly methyl ester sulfonates wherein R is on the average $C_{14}$ to $C_{16}$. The process herein is particularly useful in improving the color and purity of these preferred methyl ester sulfonates, especially potassium $C_{16}$ to $C_{18}$ methyl ester sulfonates.

The hydrophobic portion of the ester sulfonates have the sulfonate group at the α position, i.e., the sulfonate group is positioned at the carbon atom adjacent the carbonyl group. The alkyl portion of the hydrophobic portion, which corresponds to the R portion of the ester sulfonates, is on the average a $C_{10}$ to $C_{22}$ alkyl for the potassium surfactant and $C_{14}$ to $C_{22}$ alkyl for the magnesium surfactant. Preferably, the alkyl portion of this hydrophobic portion, R, is on the average a saturated straight-chain $C_{14}$ to $C_{16}$ hydrocarbon, particularly when $R_1$ is —$CH_3$.

$R_1$, forming the ester portion of the sulfonated alkyl esters, is on the average a $C_1$ to $C_8$ alkyl. Preferably, $R_1$ is on the average a $C_1$ to $C_6$ alkyl, and most preferably a $C_1$ alkyl, i.e., methyl.

When considered together, for heavy duty granular laundry detergent compositions, R and $R_1$ preferably contain a total of about 15 to 17 carbons distributed between them. Preferably the distribution is such that R is, on the average, a $C_{14}$ to $C_{16}$ alkyl and $R_1$ is methyl. For heavy duty liquid laundry and light duty liquid dishwashing detergent compositions, R and $R_1$ preferably contain a total of about 11 to 15 carbons.

The cationic portion, M, is potassium or magnesium. Generally, the cation is obtained from the agent used to neutralize the ester sulfonic acid to form the potassium or magnesium alkyl ester sulfonates.

The ester sulfonic acids, from which the ester sulfonates are prepared, can be obtained by sulfonating and then esterifying natural or synthetic fatty acids, or by sulfonating synthetic fatty acid esters. For commercial reasons the ester sulfonic acids are preferably prepared by sulfonating fatty acid esters.

Suitable fatty acid esters can be derived from unbranched $C_6$-$C_{24}$ carboxylic acids and $C_1$-$C_8$ alcohols. From an economic standpoint, the methyl esters of commercial fatty acids are preferred. Methyl esters from palm kernel oil, coconut oil or tallow oil may be used. Preferably, the fatty acid esters are hydrogenated to such an extent that their I.V. (Iodine Value) number is less than about 3.0, most preferably less than about 0.5 since sulfonation processes produce dark-colored impurities due to unsaturation in the fatty acid esters and relatively harsh requirements for sulfonation (excess $SO_3$, temperature, time, etc.). The process herein permits the use of lower grade (higher I.V. number) fatty acid esters in such sulfonation processes. Although higher I.V. number fatty acid ester result in higher levels of color bodies (dark-colored impurities) from sulfonation processes, the process herein provides the ability to remove these color bodies. Since lower grade fatty acid esters are less expensive than high grade fatty acid esters, the process herein provides an economic advantage by enabling one to use cheaper raw materials, i.e., lower grade fatty acid esters, particularly in geographies where higher grade fatty acid esters are unavailable from local suppliers.

Examples of suitable fatty acid esters include, but are not limited to, methyl laurate, ethyl laurate, propyl laurate, methyl palmitate, ethyl palmitate, methyl stearate, ethyl stearate, methyl hydrogenated tallow fatty acid ester, ethyl hydrogenated tallow fatty acid ester, methyl hydrogenated coco fatty acid ester, ethyl hydrogenated coco fatty acid ester, methyl hydrogenated palm fatty acid ester, and mixtures thereof. Preferred are hydrogenated tallow fatty acid methyl esters, hydrogenated palm oil fatty acid methyl esters, hydrogenated coconut oil fatty acid methyl esters, and mixtures thereof.

The fatty acid esters can be sulfonated to the sulfofatty acid esters by known processes, for example, by falling film or batch sulfonation. Suitable sulfonating agent include anhydrous $SO_3$, $SO_3$ diluted with nitrogen or dry air, and the like. As an example, linear esters of $C_8$-$C_{20}$ carboxylic acids can be sulfonated with gaseous $SO_3$ according to the process disclosed in "The Journal of the American Oil Chemists Society", 52 (1975), pp. 323–329.

The sulfonation of the fatty acid esters can result in the formation of dark-colored impurities in the ester sulfonic acid product, particularly if low-grade, high I.V. number fatty acid esters are utilized as the raw material in the sulfonation process. Neutralization of the ester sulfonic acid with an agent providing the cation, PI, results in an ester sulfonate surfactant composition comprising these dark-colored impurities. Generally, fatty acid esters having higher I.V. numbers result in ester sulfonates with more and darker color bodies in the surfactant composition. Additionally, it has been found that neutralization of the ester sulfonic acid with a potassium cation results in a lighter ester sulfonate surfactant composition than if the sulfonic acid had been neutralized with, e.g., a sodium cation.

The preparation of the ester sulfonate surfactant composition can also result in the formation of other undesirable impurities like soaps, and organic or inorganic sulfates salts including the sulfate and methyl sulfate salts of potassium or magnesium, and α-sulfo fatty acid disalts.

The α-sulfo fatty acid disalt impurity comprises sulfonated fatty acid salts. For example, the potassium disalt is of the formula:

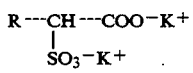

$$\begin{array}{c} R\text{---}CH\text{---}COO^-K^+ \\ | \\ SO_3^-K^+ \end{array}$$

It is theorized, although not wishing to be bound by theory, that the acid form of disalts (di-acids), are formed in the presence of water via hydrolysis reactions. During sulfonation processes, a portion of the fatty acid alkyl esters react with sulfur trioxide, $SO_3$, to form what is commonly called a mixed anhydride. The mixed anhydride reacts with water to form di-acids in a hydrolysis reaction. In another hydrolysis reaction, un-neutralized sulfonated fatty acid alkyl esters react with water to form di-acids. These di-acids form disalts upon neutralization. Disalt may also form via the direct reaction of the mixed anhydride with a base and water during the neutralization step. The formation of higher levels of disalts have also been observed during batch-type neutralization process steps. See "Surfactants in Consumer Products", pages 75–80, edited by J. Falbe, (Springer-Verlag, 1986).

The fatty acid salt impurity (commonly referred to as soaps) comprises fatty acid salts of the formula $(RCH_2COO^-)_nM^{n+}$. It is believed that soaps are formed via a hydrolysis reaction wherein un-sulfonated fatty acid alkyl esters react with water to form fatty acids. The fatty acids subsequently form soaps upon neutralization.

In addition to the impurities set forth above, other impurities may be present in the neutralized paste including sulfate and alkyl sulfate salts. It is believed that these sulfate and alkyl sulfate salts are formed as a result of reactions involving excess $SO_3$ used in the sulfonation process with other reactants or products in later process steps.

The surfactant composition forming part of the mixture in step (1) comprises a potassium or magnesium alkyl ester sulfonate surfactant and impurities formed during the preparation of the ester sulfonate surfactant. It is important that the levels of these impurities be kept to a minimum. The reduction in impurity content in the surfactant composition improves the performance and formulation flexibility of detergent compositions. These impurities, when present in the surfactant, decrease the desirable cleaning characteristics for detergent compositions when compared to compositions containing the surfactant without impurities). The dark-colored impurities cause the ester sulfonate surfactant to be aesthetically unacceptable.

In accordance with the present invention, the ester sulfonate surfactant can be separated from these impurities to provide a product having significantly lighter color and higher purity. The process of the invention herein comprises two essential steps:

(1) forming a mixture comprising water and the ester sulfonate surfactant composition; and
(2) separating the alkyl ester sulfonate surfactant from the mixture.

The first step of the process, step (1), comprises forming an aqueous mixture of the dark ester sulfonate product and water. Forming a mixture can generally be accomplished in one of two ways: low-temperature solubilization and high-temperature solubilization. Under low-temperature solubilization, the mixture formed is a heterogeneous mixture comprising water, solubilized impurities and predominantly undissolved ester sulfonate surfactant. Under high-temperature solubilization the mixture formed is a single phase, homogeneous solution comprising water, solubilized impurities and solubilized ester sulfonate surfactant.

At certain temperatures and pressures, the impurities in the surfactant composition are generally more soluble in the aqueous media than the potassium or magnesium ester sulfonate surfactant is. For example, for the potassium surfactant at ambient pressure, the combination of color bodies, sulfate and methyl sulfate salts, and disalts are readily soluble in water at temperatures above about 40° F. (4.4° C.). Potassium fatty acid (avg. R=10–12) methyl ester sulfonate surfactants, on the other hand, are relatively insoluble in water at temperatures between about 40° F. (4.4° C.) and 110° F. (43.3° C.). At temperatures above about 110° F. (43.3° C.), these ester sulfonate surfactants are readily soluble in water.

Low-temperature solubilization comprises forming a mixture comprising water, undissolved ester sulfonate surfactant, and solubilized impurities. Sufficient water in an amount relative to the ester sulfonate surfactant composition must be present to solubilize the impurities at practical processing temperatures and pressures. Concentrations and process conditions are selected to substantially solubilize, and most preferably completely solubilize the impurities. The ester sulfonate surfactant, on the other hand, remains predominantly undissolved in the mixture. Some surfactant compositions, e.g., potassium sulfonated $C_{16}$–$C_{18}$ fatty acid methyl ester surfactant compositions, may be more difficult to color improve at temperatures below about 120° F. (48.9° F.), although other impurities are removed therefrom. The selection of suitable solubilization conditions is considered to be within the ability of one of ordinary skill in the art. However, the weight ratio of water to ester sulfonate surfactant composition will generally be from about 20:1 to about 3:1, preferably from about 15:1 to about 4:1, most preferably from about 10:1 to about 5:1, at ambient pressure and temperatures from about 40° F. (4.4° C.) to about 120° F. (48.9° F.). Preferably, some shear is applied to the mixture to facilitate the solubilization of the impurities, particularly those dark-colored impurities trapped between particles of ester sulfonate surfactant. This shear can be provided through a variety of mixing devices appropriate for suspensions, e.g. stirrers, grinders, etc. Higher ratios of water to surfactant composition (greater than 20:1) can be used, but are probably not any more effective, or efficient in commercial practice.

High-temperature solubilization comprises forming a mixture comprising water, substantially dissolved ester sulfonate surfactant, and solubilized impurities. Sufficient water in an amount relative to the ester sulfonate surfactant composition must be present to solubilize the impurities and ester sulfonate surfactant at practical processing temperatures and pressures. Concentrations and process conditions are selected to substantially dissolve, and most preferably to wholly dissolve the ester sulfonate surfactant and impurities prior to separation of the alkyl ester surfactant. The selection of suitable solubilization conditions is considered to be within the ability of one of ordinary skill in the art. However, the amount of water needed to solubilize the impurities and ester sulfonate surfactant corresponds to a weight ratio of water to the ester sulfonate surfactant composition of from about 20:1 to 3:1, preferably from 15:1 to 4:1, and most preferably from 10:1 to 5:1, at ambient pressures and temperatures of between about 110° F. (43.3° C.) and 180° F. (82.2° F.). Higher ratios of water to ester sulfonate surfactant composition (greater than 20:1) can be used, but are probably not any more effective, or efficient in commercial practice.

Therefore, the mixture formed in step (1) of the process can be either a homogeneous (single-phase) mixture or heterogeneous mixture depending on whether the high-temperature or low-temperature solubilization step is utilized.

A preferred embodiment of the process forms a homogeneous mixture wherein the impurities and the ester sulfonate surfactant, i.e., the ester sulfonate surfactant composition as a whole, is completely dissolved or solubilized in the water. Since alkyl ester sulfonate surfactants are only minimally soluble below their Krafft point, the temperature of the mixture must be raised to a temperature above the blended ester sulfonate surfactant's Krafft point. For example, for palm stearin (avg. R=14–16) potassium methyl ester sulfonate surfactants, the temperature of a mixture containing a potassium methyl ester sulfonate surfactant composition must be raised to a temperature above about 120° F. (48.9° C.), preferably between about 120° F. (48.9° F.) and 180° F. (82.2° C.), to form a homogeneous solution. Since both components of the ester sulfonate surfactant composition, i.e., the ester sulfonate surfactant and the impurities, are readily soluble at temperatures above the blended surfactant's Krafft point, there is generally no need to apply more shear to the homogeneous system than that required to form a single-phase solution.

The amount of water required to solubilize the impurities can be added at any or all of the points before, during and after neutralization of the ester sulfonic acid to form the ester sulfonate surfactant composition, further discussed herein. Advantageously, some or all of the water is added during neutralization. The potassium or magnesium ester sulfonate surfactant paste formed during neutralization of the acid mix has a relatively low viscosity. Therefore, standard equipment can be used to accomplish neutralization of the acid mix. In contrast, sodium ester sulfonate surfactant pastes formed during neutralization in aqueous media are extremely viscous and often require special equipment or operating techniques.

Other solvents can be used with water to form the mixture provided that the solution of water and other solvents) is capable of substantially dissolving the impurities and provided that the ester sulfonate surfactant is capable of being separated from the mixture containing the solubilized impurities under appropriate process conditions. When a solution of water and additional solvent is used, the ratio of water to other solvents is greater than about 3:1, preferably greater than about 10:1, most preferably greater than about 30:1. Commercially relevant solvents herein are lower ($C_1$ to $C_8$) alcohols and in particular methanol. Certain processes or steps prior to the process of the invention will result in a certain amount of such solvent in the ester sulfonate surfactant composition (see below). The process of the invention herein will remove substantially all of the water-miscible solvent present in the surfactant composition.

According to particularly preferred embodiments herein, certain processes or process steps are conducted as described hereinafter.

Immediately following a sulfonation process wherein fatty acid alkyl esters are converted to ester sulfonic acids, the product of the sulfonation process is reacted with from about 3 to 20 weight % of a $C_1$ to $C_8$ alcohol. Preferably, the product stream of the sulfonation reaction is reacted with less than about 10 weight %, most preferably less than about 7 weight % of a $C_1$ to $C_8$ alcohol. Preferably, at least a portion of the alcohol is mixed with the ester sulfonic acid prior to neutralization. By premixing or reacting the ester sulfonic acid with alcohol, it has been shown in the art (See, for example, U.S. Pat. No. 4,404,143, Sekiguchi et al and copending U.S. patent application Ser. No. 07/944,854, Khan et al) that reduced levels of fatty acid all-salts are formed during neutralization, relative to systems where no reaction with alcohol is performed. It is theorized that, for example, methanol reacts with the mixed anhydride formed during sulfonation of fatty acid esters to produce the acid form of ester sulfonates and methyl sulfates thereby limiting the formation of the acid form of disalts. The present invention subsequently removes the small, residual amount of water-miscible alcohol and any alkyl sulfate impurity formed during the alcohol reaction step and present in the surfactant composition.

The process herein provides an advantage over other processes for preparing ester sulfonate surfactants when such process is conducted in conjunction with the alcohol digestion process described above. The process herein provides a means for removing a substantial amount of the residual alcohol from the surfactant without any additional process steps required. Other processes require a separate alcohol removal step, e.g., an alcohol flashing process which is a potentially dangerous and expensive process. Since water and certain lower alcohols are completely miscible liquids, a majority, if not all, of such lower alcohol will be removed from the surfactant in step (2) of the process herein, leaving a lighter-colored, higher purity potassium or magnesium alkyl ester sulfonate surfactant having little or no alcohol content.

According to other preferred embodiments, neutralization of the ester sulfonic acid is performed using potassium or magnesium alkaline salts for the potassium or magnesium surfactant, respectively, in either aqueous medium or in a substantially anhydrous medium of a lower ($C_1$–$C_8$) alcohol. These alkaline salts include KOH, $KOCH_3$, $K_2CO_3$, and $KHCO_3$, or magnesium salts such as $Mg(OH)_2$, $Mg(OCH_3)_2$, or $Mg(CO_3)_4$ $Mg(OH)_2$. $5H_2O$. A most preferred embodiment involves neutralization of the sulfonic acid using aqueous potassium or magnesium hydroxide. Neutralization of the sulfonic acid to the potassium salt of alkyl ester sulfonate results in a lighter product than other salts of alkyl ester sulfonate like sodium alkyl ester sulfonate. Additionally, this reaction is exothermic and may provide sufficient heat to raise the temperature of the product stream (an ester sulfonate surfactant composition and water) to about 120° F. (48.9° C.) or greater. Therefore, the product stream from this aqueous neutralization process step may be used directly in the first step of the invention herein. Preferably, no work-up of the product stream from the neutralization step is required and the product stream comprises a single-phase heterogeneous solution containing the surfactant composition and water wherein the solution has a temperature between about 120° and 180° F. (48.9° and 82.2° C., respectively).

An amount of water sufficient to dissolve the resultant neutralized ester sulfonate surfactant composition can be used in the preferred neutralization step. Additional water can be added after neutralization as required to improve the separation process.

The second step of the process of the present invention, step (2), comprises the step of separating the ester sulfonate surfactant from the mixture formed in step (1).

For the low-temperature solubilization system, separation can be achieved by conventional methods such as settling/clarification, centrifugation, filtration, or a combination thereof. For the high-temperature solubilization system, separation comprises precipitation of the ester sulfonate surfactant from the homogeneous solution followed by settling/clarification, centrifugation, filtration, or a combination thereof. The particular separation method or methods employed will depend upon a number of factors, such as the ratio of water to precipitated solids and the proportion of impurities which are insoluble in water versus those that are soluble or suspendable in water.

Precipitation is accomplished by driving the temperature of the homogeneous solution (the mixture) down to a temperature where the ester sulfonate surfactant is relatively insoluble in the water, but the impurities remain soluble therein, i.e., below the Krafft point of the blended alkyl ester surfactant as long as the impurities remain soluble. The selection of suitable precipitation conditions is considered to be within the ability of one skilled in the art. For example, for the potassium surfactant ($R=C_{14-16}$ and $R^1=C_1$) at ambient pressure, the solution is cooled to a temperature between about 110° F. (43.3° C.) and about 50° F. (10° C.). For the magnesium surfactant ($R=C_{14-16}$ and $R^1=C_1$), the solution is cooled to a temperature between about 100° F. (37.8° C.) and about 50° F. (10° C.). Precipitation can be performed by removing the heat from the solution, adding cool water to the solution, or a combination thereof. Heat can be removed from the solution with conventional heat transfer equipment, including plate and frame heat exchangers, shell and tube heat exchangers, etc. Adding cool water to the solution is more preferable since it requires no additional equipment to precipitate the surfactant out of the solution.

During this separation step, the ester sulfonate surfactant precipitates out of the solution while a significant amount of the dark-colored impurities and other impurities, e.g., soaps, organic and inorganic sulfates, disalts, etc. remain soluble in the water. When the ester sulfonate surfactant precipitates out, some amount of the dark-colored impurities and other impurities may precipitate out with the surfactant. Such impurities may be occluded or entrained in the surfactant. Therefore, additional processing of the surfactant may be required to obtain a surfactant that is sufficiently improved for use in consumer detergent products. For example, the ester sulfonate surfactant composition may be run through the process repeatedly, using the product stream of step (2) as the flow stream into step (1), until the desired color quality and purity of the ester sulfonate surfactant is achieved. Additional washing can also be beneficial.

Clarification can be accomplished by simple gravitation. On an industrial scale the use of conventional equipment, such as revolving plows or rakes, can be used to aid separation. Centrifugation can be by either a batch method or a continuous method, involving decantation of the supernatant from the sedimented surfactant product. Centrifugation in combination with clarification followed by washing can be usefully employed. A series of centrifuges using a counter-current supernatant washing procedure is particularly desirable.

Filtration can be performed through conventional filters. For example, on a laboratory scale, filtration, through paper, or adsorbent filters is suitable. On an industrial scale, suitable filtration equipment includes pressure filters of the plate-and-frame or shell-and-leaf construction, or of the rotating drum or disk type; vacuum or suction filters of the rotating drum or disk type; edge filters; clarification filters; etc. Filtration in combination with washing can be usefully employed.

The supernatant liquid formed during the step (2) of the process (after separating the ester sulfonate surfactant from the mixture of step (1)) comprises water and a mixture of impurities previously discussed. It has been found that this dark-colored solution containing the solubilized color bodies, organic salts, inorganic salts and disalt impurities may be treated by conventional water treatment methods, including flocculation, settling, dissolved air flotation (DAF), carbon treatment, aeration, ultra-violet light treatment, or combinations thereof, to remove the solid matter and render the water reusable in an integrated system. The solid matter (or sludge) separated from the water generally comprises some or all of the concentrated impurities.

An additional, optional step of the process herein, step (3), comprises the step of recovering the ester sulfonate surfactant from the mixture formed in step (2). Such recovery methods include, for example, evaporation of essentially all or any residual water contained in the resulting surfactant product. Evaporation may occur under normal or reduced pressure and with or without heating to yield a solid or molten ester sulfonate product that can be processed by known methods to any desired form, such as powder, flake, chunk or granulate.

On an industrial scale, water and any other solvent which may be present, can be removed by heating the mixture and flashing or evaporating the water (and solvent, if present). This can be done by any suitable method, including conventional processes, such as spray drying, atmospheric flash drying, vacuum flash drying, drum drying, wiped or transported film evaporation, or a combination thereof. Spray drying can be used to directly yield an ester sulfonate surfactant in powdered or granular form. The other methods yield ester sulfonate products in a chunk, noodle, or large particulate form, which can be further processed by known methods to any desired form, for example, milling to a granular form, or flaking and then chopping or milling to a granular form. The water which is removed to recover the ester sulfonate surfactant can be condensed, recovered and recycled for re-use in any of the water-addition steps described herein.

The separation step (2) and recovery step (3) can be performed simultaneously if desired. For example, a heterogeneous mixture can be passed through a pressure filter or centrifuge with optional washing wherein the surfactant is separated and recovered essentially simultaneously. The ester sulfonate surfactant can also be recovered with a certain amount of water in a paste form and used directly in an agglomeration process with other detergent components to form a detergent granule.

As a result of this process, potassium and magnesium ester sulfonate surfactants of improved purity are obtained. The process also results in surfactants of improved color. This improvement in color can be measured in two ways: the color improvement in the surfactant per se (exhibited in an increase in Hunter L numbers and/or decrease in the absolute value of Hunter, a, and b numbers) or color improvement of the surfactant in wash water (exhibited in a decrease of the Klett color numbers). Where the process involves running the surfactant composition through the process several times, the resultant product is near-white in color, contains less impurities, and can be used directly in cleansing and washing agents and products.

The process further allows for greater flexibility in the raw materials and process conditions of sulfonation. Starting materials having a greater degree of impurities themselves which can result in the formation of dark-colored impurities, or processing conditions for obtaining greater rates of conversion to the ester sulfonate, may be used without the ,concerns heretofore associated with the need for bleaching. Impurities which can result in the formation of dark-colored impurities are known in the art, and include Oxo compounds, glycerine, glyceride (mono-,di- or tri-) and unsaturated fatty acid ester. By avoiding the need for bleaching, the process may also avoid the formation of sensitizers, such as those described in D. Connor et al.; *Identification of Certain Sultones as the Sensitizers in an Alkyl Ethoxy Sulfate*, "Fette Seifen Anstrichmittel" 77, 25–29 (1975).

The ester sulfonate surfactant products obtained by the method of the present invention are useful as active ingredients for cleansing and washing agents and products, and can be employed in admixture with other surfactants. For example, in detergent compositions, suitable co-surfactants include anionic surfactants, nonionic surfactants, cationic surfactants, zwitterionic surfactants or amphoteric surfactants. Other ingredients conventionally used in detergent formulations may also be used. Such ingredients include those generally used as builders, enzymes, bleaching agents and activators, soil release agents, chelating agents, soil-removal and anti-redeposition agents, dispersing agents, brighteners, suds suppressors, etc. Alternatively, the potassium and magnesium ester sulfonate surfactants may be solubilized at low washing temperatures by counter ion exchange with other salts, e.g., a sodium salt.

The following non-limiting examples illustrate the invention and facilitate its understanding. All parts and percentages herein are by weight unless otherwise stated. All color measurements were carried out using a Hunter Colorimeter providing L, a, b readings for solids or a Klett-Summerson Photo Electric Colorimeter (Model 900-3) at 400-450 nm for liquids.

EXAMPLE I

Ester sulfonic acid is produced by conventional sulfonation of palm stearin fatty acid methyl ester. The acid component of the methyl ester consists essentially of saturated fatty acids with an Iodine Value of 0.28 and the following chain length distribution (by weight percent):

|     |      |
| --- | ---- |
| $C_{12}$ | 0.2  |
| $C_{14}$ | 1.5  |
| $C_{16}$ | 65.4 |
| $C_{18}$ | 32.2 |
| $C_{20}$ | 0.7  |

The sulfonation reaction is carried out at about 40° C. in an annular falling film reactor using a mixture of sulfur trioxide and air ($SO_3$ content: 5% by volume; $SO_3$ excess: 25 mole percent). The sulfonated methyl ester acid mix is then digested in a closed vessel for 35 to 40 minutes at a temperature of 80° C. to 90° C. The degree of sulfonation after digestion is about 93%.

This acid mix is then reacted with 16% methanol, by weight of the acid mix. The reaction is conducted for 40–50 minutes at a temperature of approximately 80° C. in a closed vessel, in-line. The resultant acid mix has a Klett color (5%) of approximately 10,000.

The acid mix is then neutralized with a 10% w/w solution of KOH in water at a temperature of about 45° to 55° C. To maintain fluidity during neutralization, additional methanol is added. The solid content of the neutralized product is determined (by Cenco drying an aliquot) to be 38.5%. A portion of the neutralized product is dried and ground to a powder. The color of this dried sample is L=71.3, a=2.4, b=14.1. Percent volatiles of the sample is 2-3% (by Cenco drying) consisting essentially of incidental moisture.

A second portion of the wet, neutralized paste (181.8 gram containing 70 grams dry solids) is added to 818.2 grams deionized water to form a 7% w/w solids mixture. This mixture is then heated with mixing to a temperature of 165° F. (73.9° C.) and forms a single-phase homogeneous solution. Upon cooling to 53° F. (11.7° C.) the solution forms a two-phase mixture.

The mixture is centrifuged in a large laboratory centrifuge for 1 hour at the high setting. Upon centrifugation, the mixture separates easily into two layers. The top layer is a darkly colored aqueous layer, and the bottom layer is a light brown pasty sludge. These two layers are then recovered (with the addition of another 30 grams of deionized water to rinse solids clinging to jars) as follows: wet sludge=569 grams; dark liquor=441 grams; loss on glassware/tubes=20 grams.

A portion of this potassium neutralized surfactant composition (about 45 grams of solids in about 500 ml water) is further purified by a filtration procedure as follows:

About 600 ml of water is added to the surfactant composition and the resulting mixture is stirred to form a heterogeneous slurry. The sample is then heated to 130° F. (54.4° C.) to completely solubilize the surfactant composition. The ester sulfonate surfactant is precipitated by cooling the solution to about 70° F. (21.1° C.) to form a heterogeneous mixture. The mixture is then separated via gravimetric filtration on a Whatman #40 ashless filter paper. The water soluble distillates (dark brown colored liquids) are collected and evaporated to dryness and show a high level of impurities including disalts, potassium sulfate, potassium methyl sulfate and soaps. The water insoluble fractions (precipitated fractions) remain on the filter paper and are collected. This process is repeated using the collected precipitates. Each purification procedure yields a product of visibly improved (i.e., lighter) color. Repeating the procedure four times provide a white colored paste.

The resulting product is dried at about 70° F. (21.1° C.) under reduced pressure. After drying, 33.3 grams of a fine white powder is isolated and the paste layers are dried and analyzed for surfactant purity, Klett Color (calculated) and Hunter Colorimeter color (see Table 1). The white powder is characterized as high purity potassium methyl ester sulfonate by NMR methods. The results indicate significant improvement in purity of the recovered surfactants. Additionally, color is significantly improved for the product.

TABLE 1

| Component | Unpurified Surfactant Composition (% by weight) | Purified White Powder (% by weight) |
| --- | --- | --- |
| Potassium methyl ester sulfonate | 84.4 | 93.6 |
| Potassium disalt | 1.6 | 0.7 |
| Water | 3.3 | 4.4 |
| $K_2SO_4$ | 2.4 | 0.6 |
| $K(CH_3)SO_4$ | 7.7 | 0.6 |
| Unreacted methyl ester | 0.7 | 0.4 |
| Soap | 0.4 | 0.1 |
| Color Analysis | | |
| Hunter Color (dried, ground solids) | | |
| L | 71.3 | 91.6 |

TABLE 1-continued

| Component | Unpurified Surfactant Composition (% by weight) | Purified White Powder (% by weight) |
|---|---|---|
| a | 2.4 | 0.4 |
| b | 14.1 | 6.6 |
| Klett Color of dried solids, dissolved in 0.1% solids solution. | 119 | 14 |

EXAMPLE II

Sulfonated methyl ester acid mix is prepared from the same palm stearin fatty acid methyl ester stock used in Example I, using substantially the same process described therein.

Neutralization of the acid mix is performed with KOH pellets dissolved in methanol at 10% w/w concentration. The neutralization process is conducted in a continuous, closed loop, dominant bath system. The amount of recycled neutralized product to the amount removed from the loop is 15–20 to 1. The acid mix and base are pumped simultaneously into the shear zone of a high shear driven mixer (Ross Model ME 400 L at 10,000 rpm) and at precise proportions so as to maintain an essentially neutral pH of 6 to 8 in the finished product paste. The finished product is trimmed with a 10% KOH/methanol solution to pH 6.9.

The finished product paste is then dried in a vacuum oven at 35–40° C. under a vacuum of 28–29 inches of Hg. The resultant product is a dark-colored potassium methyl ester sulfonate surfactant composition having a Klett color (0.1% solution in water) of 106.

Two 50 gram samples of the dried surfactant powder are each added to about 600 grams deionized water at ambient temperature (72° F., 22° C.) to form 7.7 weight % mixtures. The first mixture (Sample 2A) is agitated with a laboratory Lighting Mixer and cooled to 45° F. (7° C.). Once the temperature of 45° F. (7° C.) is attained, vigorous mixing is continued for 10 minutes and the temperature maintained. Under these conditions, the ester sulfonate surfactant is incompletely dissolved although the color bodies are somewhat solubilized.

The second mixture (Sample 2B) is heated to 130° F. (54° C.) while under agitation as above. During this operation the surfactant composition is completely dissolved. The solution is then allowed to cool to ambient temperature, and then further cooled to 45° F. (7° F.)

Samples 2A and 2B are then subjected to "Batch Centrifugation" in a DuPont Sorvall Model SS-3 automatic centrifuge, at 11,000 RPM for 15 minutes. Following centrifugation, both samples separate into two distinct layers: a "paste layer" consisting primarily of refined ester sulfonate surfactant and entrained liquor, and a "liqueur layer" consisting primarily of water and dissolved impurities. These two layers are physically separated and weighed.

The paste layers are dried and analyzed for surfactant purity, Klett Color (calculated) and Hunter Colorimeter color (see Table 2). The results indicate significant improvement in purity of the recovered surfactants. Additionally, color is significantly improved for Sample 2B although not for Sample 2A.

TABLE 2

| Component | Unpurified Surfactant Composition | Sample 2A (72° F.) (% by weight) | Sample 2B (129° F.) |
|---|---|---|---|
| Potassium methyl ester surfactant | 80.4 | 90.8 | 91.7 |
| Potassium disalt | 6.1 | 3.7 | 2.9 |
| Water | 0.3 | 2.9 | 4.0 |
| $K_2SO_4$ | 1.6 | 0.5 | 1.4 |
| $K(CH_3)SO_4$ | 12.6 | 0.7 | 0.8 |
| Color Analysis | | | |
| Hunter Color (Dried, ground solids) | | | |
| L | 73.9 | 74.1 | 84.1 |
| a | 1.8 | 1.8 | 0.8 |
| b | 11.1 | 11.5 | 9.2 |

Two additional samples (75 grams each) of the dried surfactant powder used to make Samples 2A and 2B are added to 900 grams of distilled water to form 7.7 weight % mixtures. The temperature of the distilled water for one mixture (Sample 2C) is 88° F. (31° C.). The temperature of the mixture is maintained at this temperature while it is vigorously mixed with a laboratory Ross high shear mixer Model ME100L operating at about 200–300 rpm for 20 minutes. The temperature of the distilled water for the other mixture (Sample 2D) is 118° F. (48° C.). The temperature of this mixture is maintained at 118° F. (48° C.) while it is also vigorously mixed with a laboratory Ross high shear mixer Model ME100L operating at about 200–300 rpm for 20 minutes. A portion of each of these samples is purified, separated and recovered by the DuPont Sorvall batch centrifuge process described above. Following centrifugation, temperatures of the dark liquid layers for the samples equilibrate to about 90° F. (32° C.). The paste layer in each sample is dried and analyzed for Klett color and Hunter Colorimeter color. The results indicate significant improvement in purity for both recovered surfactants and a significant Hunter color improvement for Sample 2D. The results also show Klett color improvements for both samples (dried solids in 0.1% solids solution).

EXAMPLE III

A potassium methyl ester sulfonate surfactant composition is prepared from a $C_{12-14}$ fatty acid methyl ester feed stock via conventional sulfonation, digestion and neutralization processes. After drying, the surfactant composition is a dark-colored methyl ester sulfonate surfactant composition. This surfactant composition is subjected to the same process described for Sample 2B above including dissolving the surfactant composition in deionized water at an elevated temperature under agitation, cooling, and centrifugation. The resultant surfactant product exhibits improved color and purity.

EXAMPLE IV

A high Iodine Value methyl ester feedstock is prepared by blending several stock methyl esters having various chain lengths and Iodine Values such that the blended feedstock has the following analysis and chain length distribution: Iodine Value=1.9; $C_{12}=0.6\%$; $C_{14}=2.8\%$; $C_{16}=-65.1\%$; $C_{18}=31.2\%$; $C_{20}=0.3\%$. R for the methyl ester starting material, therefore, is on the average 14.6. $R_1$ is methyl.

The sulfonation reaction is carried out at about 40° C. in an annular falling film reactor using a mixture of sulfur trioxide and air ($SO_3$ content: 5% by volume;

SO3 excess: 40% mole percent). The sulfonated methyl ester acid mix is then digested in a closed vessel for 45 minutes at a temperature of 87° C. The degree of sulfonation is about 90%.

The digested acid mix is then reacted with 12% methanol, by weight of the acid mix, in accordance with the methanol reaction process step described in Example I above. Following sulfonation, digestion and reaction with methanol, the acid mix has a Klett color (5% solution) of about 31,500.

Neutralization of the acid mix is performed with KOH pellets dissolved in methanol in a manner similar to the neutralization process step described in Example II above, except that the neutralization is conducted on a small batch basis in the laboratory. The acid mix and methanol are added to the reaction vessel and the basic KOH/methanol solution is slowly added into the shear zone of a Ross Mixer (Model ME 100L). Neutralization is continued until the pH rises to between 6 and 8. After neutralization, the mixture is dried in a vacuum oven to yield a dried non-purified potassium methyl ester sulfonate powder having a Hunter Color of: L=63.9; a=2.3; b=11.1.

The neutralized dried surfactant powder is solubilized and centrifuged in the same way that the dried surfactant powder samples of Example II are except that the paste layer formed from the sample herein is recovered and reconstituted with water into a second 10% solution and then solubilized and centrifuged a second time.

The resultant purified wet paste is recovered, dried and ground prior to analysis. See Table 3.

TABLE 3

| Component | Unpurified Surfactant Composition (% by weight) | Purified Surfactant |
|---|---|---|
| Potassium methyl ester sulfonate | 84.3 | 91.3 |
| Potassium disalt | 2.0 | 1.5 |
| Water | 2.0 | 4.2 |
| K2SO4 | 1.9 | 0.5 |
| K(CH3)SO4 | 6.5 | 2.0 |
| Physical Analysis | | |
| Hunter Color (Dried, ground solids) | | |
| L | 63.9 | 73.6* |
| a | 2.3 | 1.4 |
| b | 11.1 | 9.4 |
| Klett Color of Dried solids, Dissolved in 0.1% solids soln. | 450 | 98 |

*Hunter Color on sample dried to about 0.5% moisture.

EXAMPLE V

Sulfonated methyl ester acid mix is prepared from the same palm stearin fatty acid methyl ester stock used in Example I, using substantially the same process described therein.

Neutralization of the acid mix is performed with Mg(OCH3)2 at 8% concentration w/w in methanol. The neutralization process is conducted in a small batch reactor wherein Mg(OCH3)2 solution is continuously added via the shear zone of a Ross mixer (Model ME100L) to the acid mix and a small amount of methanol in the reactor. Final pH (1% aqueous solution) of the neutralized product is 6.7, and Cenco solids is 44%.

The product of this reaction is dried to remove volatiles and ground into a dried powder. The dried powder is subjected to a filter funnel wash. 50 grams of the dried non-purified powder comprising magnesium methyl ester sulfonate surfactant is added to 450 grams distilled water. The mixture is heated to solubilize the powder completely, and then cooled to about 80° F. (27° C.), whereupon precipitation occurs resulting in a two phase mixture. The two phase mixture is filtered to recover the precipitate on filter paper, and repeatedly washed with ambient temperature distilled water. The recovered precipitate is dried, ground into a powder and analyzed for color improvement. See Table 4. The results indicate a significant color improvement for the resultant surfactant product.

TABLE 4

| Color Analysis | Unpurified Surfactant Composition | Purified Surfactant |
|---|---|---|
| Hunter Color (Dried, ground solids) | | |
| L | 49.6 | 76.6 |
| a | 3.1 | 1.7 |
| b | 11.0 | 11.6 |
| Klett Color of Dried Solids Dissolved in 0.1% solids soln. | 134 | 67 |

What is claimed is:

1. A process for improving an alkyl ester sulfonate surfactant composition, said surfactant composition comprising:

(i) an alkyl ester sulfonate surfactant of the formula

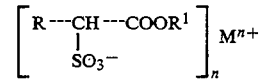

$$\left[ \begin{array}{c} R-CH-COOR^1 \\ | \\ SO_3^- \end{array} \right]_n M^{n+}$$

wherein: (1) R is on the average a $C_{10}$ to $C_{22}$ alkyl, $R^1$ is on the average a $C_1$ to $C_8$ alkyl and n=1 when M is potassium; or (2) R is on the average a $C_{14}$ to $C_{22}$ alkyl, $R^1$ is on the average a $C_1$ to $C_8$ alkyl and n=2 when M is magnesium; and (ii) impurities formed during the preparation of said alkyl ester sulfonate surfactant;

said process comprising the steps of:

(1) forming a mixture comprising:
        (a) said alkyl ester sulfonate surfactant composition; and
        (b) water in an amount sufficient to substantially solubilize said impurities; and
    (2) separating said alkyl ester sulfonate surfactant from said mixture wherein the temperature of said mixture is from about 4° C. to below the Krafft point of said surfactant, thereby forming a heterogeneous mixture comprising dissolved impurities and undissolved ester sulfonate surfactant.

2. The process of claim 1 wherein R for said alkyl ester sulfonate is on the average a $C_{10}$ to $C_{16}$ alkyl, $R^1$ is on the average a $C_1$ to $C_6$ alkyl and M is potassium.

3. The process of claim 1 wherein R for said alkyl ester sulfonate is on the average a $C_{14}$ to $C_{16}$ alkyl, $R^1$ is on the average a $C_1$ to $C_6$ alkyl and M is potassium.

4. The process of claim 3 wherein $R^1$ for said alkyl ester sulfonate is methyl.

5. The process of claim 1 wherein R for said alkyl ester sulfonate is on the average a $C_{14}$ to $C_{16}$ alkyl, $R^1$ is methyl and M is magnesium.

6. The process of claim 1 wherein said impurities comprise dark-colored impurities.

7. The process of claim 1 wherein said impurities comprise organic and inorganic sulfate salts, α-sulfo fatty acid disalts, and soaps.

8. The process of claim 6 wherein said impurities further comprise organic and inorganic sulfate salts, α-sulfo fatty acid disalts, and soaps.

9. The process of claim 1 wherein some shear is applied to said mixture to facilitate the solubilization of said impurities.

10. The process of claim 1 wherein step (1) comprises adding said water such that the temperature of said mixture is between about 43.3° C. and 82.2° C. thereby forming a homogeneous mixture comprising dissolved impurities and substantially dissolved ester sulfonate surfactant.

11. The process of claim 1 wherein the weight ratio of water to alkyl ester sulfonate surfactant composition in said mixture in step (1) is from about 20:1 to about 3:1.

12. The process of claim 8 wherein the weight ratio of water to alkyl ester sulfonate surfactant composition in said mixture in step (1) is from about 20:1 to about 3:1.

13. The process of claim 8 wherein the weight ratio of water to alkyl ester sulfonate surfactant composition in said mixture in step (1) is from about 10:1 to about 5:1.

14. The process of claim 11 wherein the weight ratio of water to alkyl ester sulfonate surfactant composition in said mixture in step (1) is from about 10:1 to about 5:1.

15. The process of claim 1 wherein step (2) comprises centrifugation or filtration of said ester sulfonate surfactant from said mixture of step (1), or a combination thereof, or in combination with washing.

16. The process of claim 1 wherein step (2) comprises centrifugation or filtration of said ester sulfonate surfactant from said mixture of step (1), or a combination thereof, or in combination with washing.

17. The process of claim 1 wherein step (2) comprises precipitation of said ester sulfonate surfactant from said mixture of step (1) followed by centrifugation or filtration of said surfactant, or a combination thereof, or in combination with washing.

18. The process of claim 10 wherein step (2) comprises precipitation of said ester sulfonate surfactant from said mixture of step (1) followed by centrifugation or filtration of said surfactant, or a combination thereof, or in combination with washing.

19. The process of claim 1 further comprising: (3) recovering said alkyl ester sulfonate surfactant.

20. The process of claim 15 further comprising: (3) recovering said alkyl ester sulfonate surfactant.

21. The process of claim 16 further comprising: (3) recovering said alkyl ester sulfonate surfactant.

22. The process of claim 17 further comprising: (3) recovering said alkyl ester sulfonate surfactant.

23. The process of claim 18 further comprising: (3) recovering said alkyl ester sulfonate surfactant.

24. The process of claim 19 wherein step (3) comprises evaporating any water remaining in said surfactant, agglomerating said surfactant with other detergent ingredients to form a detergent granule, or a combination thereof.

25. The process of claim 24 wherein steps. (2) and (3) are performed simultaneously.

26. The process of claim 1 wherein said alkyl ester sulfonate surfactant is obtained by neutralizing an ester sulfonic acid with an alkoxide of the formula $(R^2O^-)_nM^{n+}$, wherein $R^2$ is H or a $C_1$-$C_8$ alkyl, in an aqueous medium.

27. The process of claim 1 wherein said alkyl ester sulfonate surfactant is obtained by neutralizing an ester sulfonic acid with an alkoxide of the formula $(R^2O^-)_nM^{n+}$, wherein $R^2$ is H or a $C_1$-$C_8$ alkyl, in a substantially anhydrous medium of a lower alcohol.

28. The process of claim 1 wherein said alkyl ester sulfonate surfactant is obtained by reacting an ester sulfonic acid with from about 3 to 20 weight % of a $C_1$ to $C_8$ alcohol, followed by neutralizing said ester sulfonic acid with an alkoxide of the formula $(R^2O^-)_nM^{n+}$, wherein $R^2$ is H or a $C_1$-$C_8$ alkyl, in an aqueous medium.

29. The process of claim 1 wherein said alkyl ester sulfonate surfactant is obtained by reacting an ester sulfonic acid with from about 3 to 20 weight % of a $C_1$ to $C_8$ alcohol, followed by neutralizing said ester sulfonic acid with an alkoxide of the formula $(R^2O^-)_nM^{n+}$, wherein $R^2$ is H or a $C_1$-$C_8$ alkyl, in a substantially anhydrous medium of a lower alcohol.

30. The process of claim 28 wherein said surfactant composition further comprises a $C_1$ to $C_8$ alcohol in an amount such that the weight ratio of water to alcohol in step (1) is greater than about 3:1.

31. The process of claim 29 wherein said surfactant composition further comprises a $C_1$ to $C_8$ alcohol in an amount such that the weight ratio of water to alcohol in step (1) is greater than about 3:1.

32. The process of claim 30 wherein the weight ratio of water to alcohol in step (1) is greater than about 30:1.

33. The process of claim 28 wherein said sulfonic acid is obtained by sulfonating fatty acid esters having an Iodine Value less than about 3.

34. The process of claim 28 wherein said sulfonic acid is obtained by sulfonating fatty acid esters having an Iodine Value less than about 0.5.

35. The process of claim 29 wherein said sulfonic acid is obtained by sulfonating fatty acid esters having an Iodine Value less than about 3.

36. The process of claim 29 wherein said sulfonic acid is obtained by sulfonating fatty acid esters having an Iodine Value less than about 0.5.

37. The process of claim 1 further comprising a pre-step before step 1, wherein the temperature of said surfactant is above its Krafft point.

* * * * *